United States Patent

Barabash et al.

Patent Number: 5,860,926
Date of Patent: Jan. 19, 1999

[54] METHOD AND ULTRASOUND APPARATUS FOR FAST ACQUISITION OF TWO DIMENSIONAL IMAGES

[76] Inventors: Leonid S. Barabash, 13021 S. 48th St., Apt. 2097; Aaron E. LaBarge, 3914 E. Nambe St., both of Phoenix, Ariz. 85044; Angel T. M. Wang, 391-G, Cannon Green Dr., Goleta, Calif. 93117

[21] Appl. No.: 910,485

[22] Filed: Jul. 25, 1997

[51] Int. Cl.$^6$ ........................................... A61B 8/00
[52] U.S. Cl. ........................... 600/443; 600/459; 342/25
[58] Field of Search .................................. 600/443, 441, 600/459, 458; 342/25, 179; 367/7

[56] References Cited

U.S. PATENT DOCUMENTS

5,617,862  4/1997  Cole et al. ............................. 600/459

*Primary Examiner*—Marvin M. Lateef
*Assistant Examiner*—Ali Imam

[57] ABSTRACT

The present invention consists of a method for a fast acquisition of two dimensional images by the use of synthetic transmit and receive apertures formed in the schematics with cross transducers and can be used for the reconstruction of three dimensional images. The method of a fast two dimensional image acquisition preserves the flat beam generation and irradiation of the sector of an investigated part of a human body by a single transmit array. Simultaneously, a switching of transmit (or receive) arrays and irradiation of the same sector of a human body by different transmit arrays with a consequent fine shifting and summation of the received and digitized information in the region of interest provides an additional focusing of the transmit (or receive) beam along the coordinate parallel to the flat beam plane. The schematics of transducers for the realization of this method are described. The suggested method works with digital beamformer schematics, when echo signals from every individual element of the receive arrays are amplified, digitized and stored in memory.

4 Claims, 6 Drawing Sheets

View A — 113 b)

View A — 113

Figure 6

METHOD AND ULTRASOUND APPARATUS FOR FAST ACQUISITION OF TWO DIMENSIONAL IMAGES

DESCRIPTION

1. Field of the Invention

The present invention consists of a method for a fast two dimensional image acquisition and ultrasound transducers for investigations of human body structures. More precisely, the invention consists of a method of using synthetic transmit and receive apertures for a fast two dimensional image acquisition and some versions of a cross transducer, which allows transmission and reception of electronically scanned acoustic beams and two dimensional reconstruction of real-time anatomical images.

2. State of the Art

U.S. patent application Ser. No. 08/742403 of L. S. Barabash et al. discloses methods and an ultrasound apparatus which receives three dimensional images from an electronically processed pencil acoustic beam formed by a cross array transducer. The pencil acoustic beam is electronically processed from two or more flat acoustic beams which are electronically scanned by two or more crossed arrays. The arrays have axial symmetry and cross at an optimal angle. The associated electronic systems for transmit and receive arrays are completely separate, including the ground electrodes. One system of arrays is dedicated to ultrasound signal transmission, the other one is dedicated to reception of reflected ultrasound signals. This design allows us to reconstruct three dimensional images of anatomic structures.

A fast method of three dimensional image reconstruction is described by Barabash et al. This method employs the property of flat acoustic beam generated by one transmit array to irradiate a sector of an investigated part of a human body. Reflected echo signals from this sector of a human body are received by individual elements of one or more receive arrays. The amplitude and time information from every receive array individual element is amplified, digitized and stored in memory. Fast reconstruction of parts of acoustic lines for the irradiated sector of investigated object is realized in the memory of the apparatus by a shift of digitized information with delays to form necessary receive apertures which scan the irradiated sector, and a consequent summation of amplitude information for every scan angle in some time interval corresponding to the width of receive zone. All acoustic lines for a part of a two dimensional image with a set transmit focal distance and within the limits of the possible scan angles can be reconstructed by the use of the digitized information registered from one acoustic pulse. The same steps for reconstruction of the image for other transmit zones are used. As a result, a two dimensional acoustic image is reconstructed during the time necessary for the generation and propagation of acoustic wave pulses with number is equal to the number of transmit zones. This method allows fast reconstruction of two dimensional acoustic images and, consequently, three dimensional acoustic images also. However, a lower level of side lobe peak amplitudes can be obtained if more than one transmit arrays are used. But, in this case, we lose the ability to use the fast method of reconstruction of acoustic images for a crossed placement of transmit arrays. It happens because flat transmit beams generated by crossed transmit arrays irradiate different sectors of a human body and only the part of a human body irradiated by the shaped "pencil" acoustic beam can be reconstructed.

Another problem is that the cross transducer suggested by Barabash et al. has severe requirements on the level of noise in the signal receiving electronics, which defines by a small size of array individual elements. It is possible to obtain further rejection of the side lobe amplitudes and increased gain in the acoustic power by increasing the number of arrays in the transmit and receive systems. But we forfeit the use of the method for fast acquisition of two dimensional images as it was stated before.

Cross transducers with multiple parallel transmit and receive arrays are described in the U.S. Patent application Ser. No. 08/802757 of L. Barabash. Such kind of transducer improve the imaging of human body structures near the surface of the transducer, but the requirements for radiated acoustic power, level of side lobes and noise of reception channels are left the same as for the transducers described in the paragraph above.

SUMMARY OF INVENTION

The present invention consists of a method for a fast acquisition of two dimensional images by the use of synthetic transmit and receive apertures for schematics with cross transducers and can be used for reconstruction of two and three dimensional acoustic images. The method preserves the flat beam generation and irradiation of the sector of a human body by a single transmit array. Simultaneously, switching of transmit (or receive) arrays placed in parallel and irradiated the same sector of a human body with a consequent shifting and summation of the recorded information in the region of interest provides an additional focusing of the transmit (or receive) beam along the coordinate parallel to the flat acoustic beams. This method requires a time longer than described above by a factor equal to the number of transmit arrays, but provides an additional reduction of the side lobes peak amplitudes and an increase of the radiated acoustic power.

The schematics of transducers for the realization of this method are described. The suggested method works with digital beamformer schematics, when echo signals from every individual element of the receive arrays are amplified, digitized and stored in memory.

BRIEF DESCRIPTION OF THE DRAWINGS

These features and advantages of the present invention will be better seen by reference to the detail description with accompanying drawings wherein.

DETAILED DESCRIPTION

The method of a fast acquisition of two dimensional images supposes a use of the cross transducer with more than one transmit array and one or more receive arrays. All transmit arrays can emit flat acoustic beams with the same focal point by the adjustment of the array individual element delays. Transmit arrays are placed in parallel with each other, so flat acoustic beams are generated at the same plane and irradiate the same sector of an investigate part of a human body. If more than one receive array is used, they are placed in parallel each other and at some angle to transmit arrays, and have the flat beam apertures, which cross with flat transmit beams and receive reflected echo signals from the same irradiated sector of a human body. The receive flat apertures can scan the irradiated sector of a human body by the adjustment of the receive array individual element delays.

If we will study the behavior of the delays of the individual elements of transmit (or receive) arrays for the different scan angles we can notice that the difference of delays for the same number of individual elements of different arrays is almost constant for fixed scan angle. This difference defines by a ratio of a focal distance and a pitch of arrays ( a distance between centers of the same number of individual elements of different arrays). The difference of delays for the same number of individual elements is noticeable for small focal distances and decreases with a focal distance rise. However, if we'll take into account a finite time interval of a quantization of transmit individual element delays, we can assume that the difference of delays for the same number of individual elements is constant. In other words, the change of the scan angle leads to a parallel shift of transmit or receive apertures in time without the change of the shape of the apertures.

Figure 1:
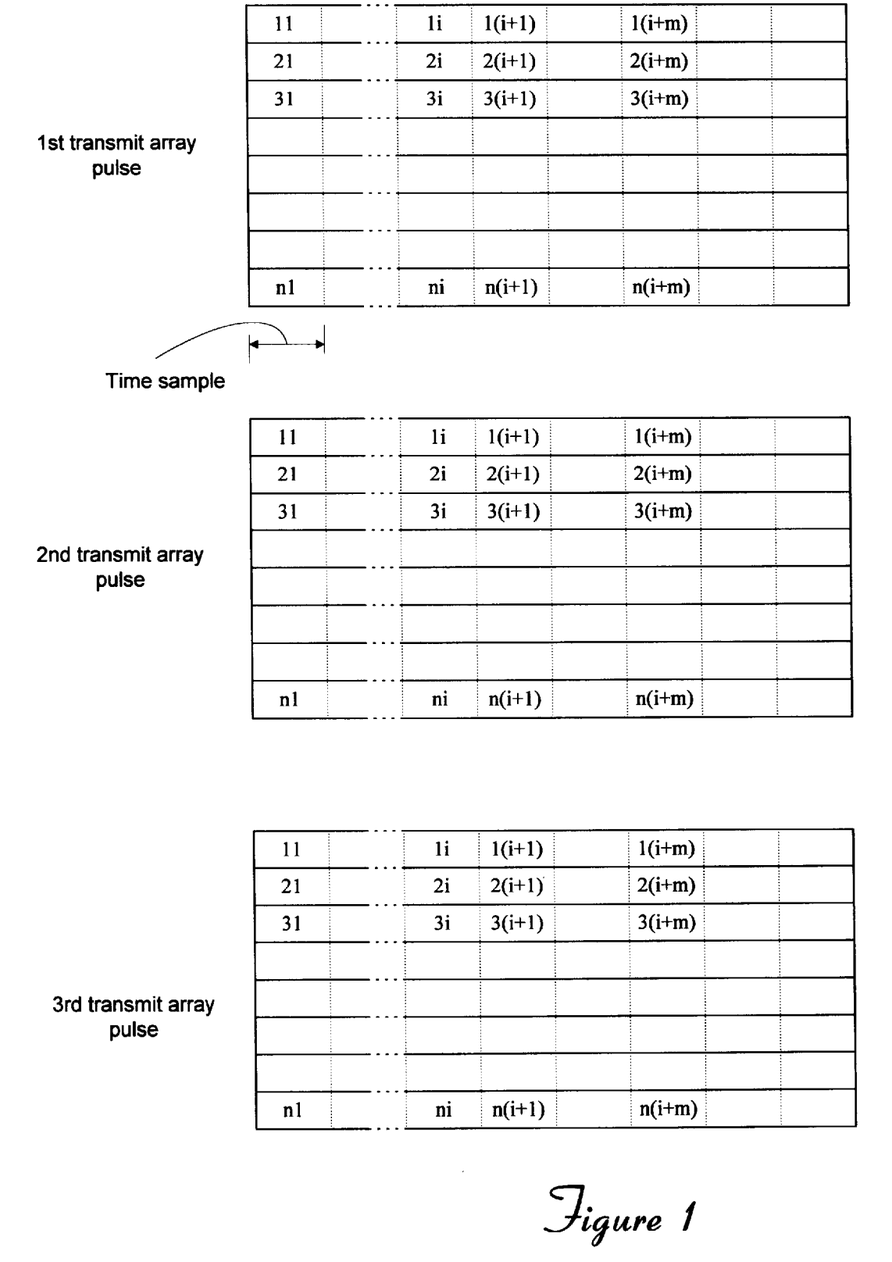
FIG. 1 presents an information map contents recorded digitized amplitudes of echo signals of receive array individual elements for the different transmit array triggers. An event with three transmit arrays is shown at FIG. 1.

Thus, the use a feature that the difference in delay of transmit arrays is constant makes it possible to realize synthetic transmit apertures. Transmit arrays can be switched in time and generate their flat acoustic beams in succession. The echo signals from acoustic pulse of each transmit array for the set focal distance are received by receive array individual elements. An information from every receive individual element is amplified, digitized and stored in memory. FIG. 1 shows this step of the method for transducer with three transmit and one receive arrays. Information map contains three parts. The first part is recorded after emitting of the acoustic flat beam by the first transmit array. The map rows contain amplitudes from every receive individual element digitized with some time sample as is shown at FIG. 1. Amplitudes 11, 12, 13, . . . 1i, 1(i+1), . . . 1(i+m) were registered by the first individual element of the receive array, 21, 22, 23, . . . 2i, . . . 2(i+m) by the second one and etc. Amplitudes n1, . . . ni . . . n(i+m) belong to the last individual element of the receive array.

The second part of the information map contains amplitudes recorded from receive individual elements after generation of flat acoustic beam by second transmit array and digitized information received from third transmit array acoustic pulse is stored in third part of the map. As a result, we obtained three sets of information necessary for acquisition of a part of a two dimensional image of the irradiated sector of a human body for a given transmit focal zone.

Figure 2:
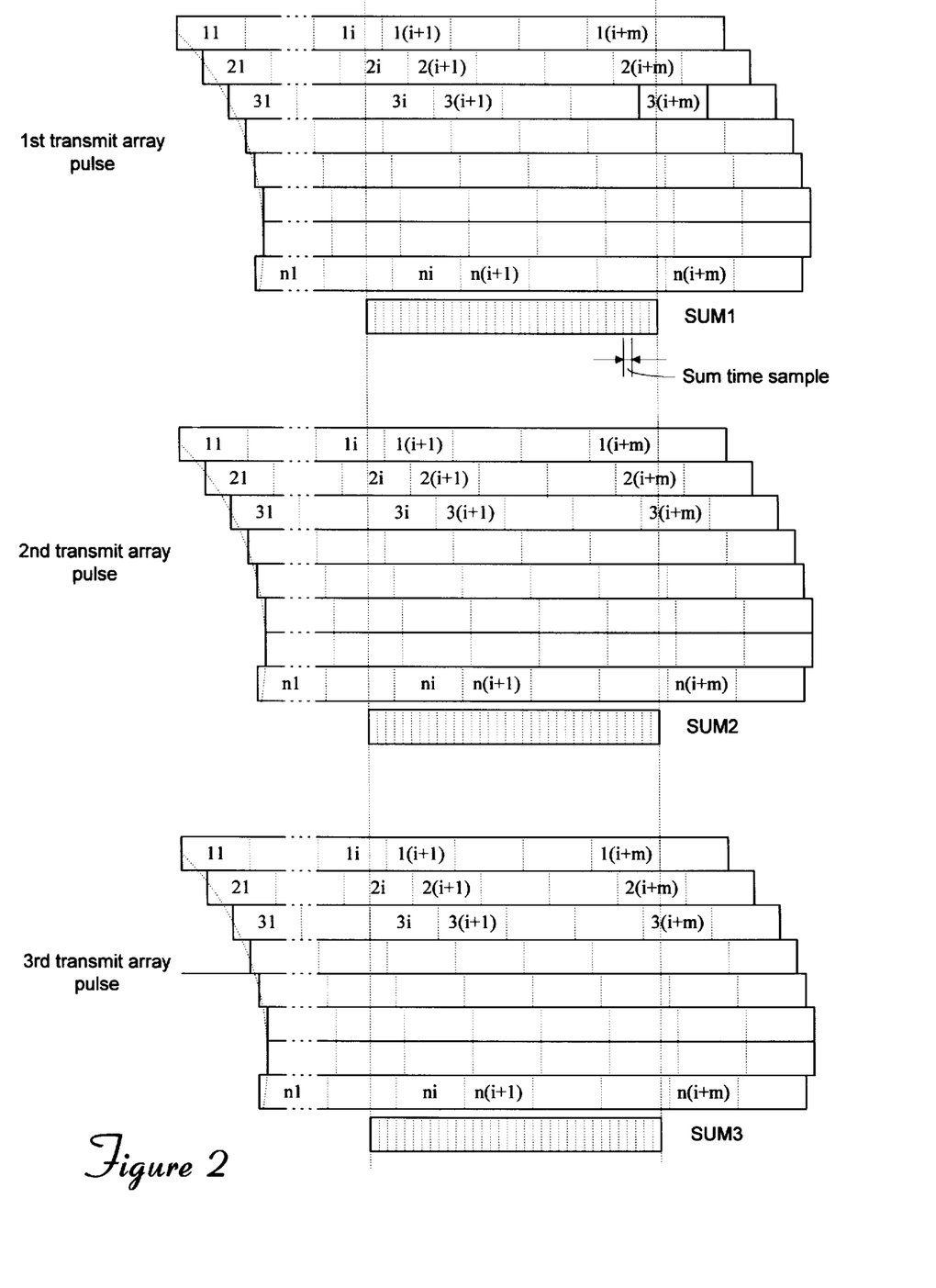
FIG. 2 shows the next step of the method of a fast acquisition of two dimensional images: creation of the synthetic receive apertures and summation of the amplitude information for different transmit array pulses.

FIG. 2 shows the next step of the realization of the fast method of two dimensional image acquisition: creation of the synthetic receive apertures for parts of information recorded from the different transmit array pulses. Row information from different receive individual elements shifts for the necessary number of time samples to create receive apertures for the set focal point. The size of time sample shifts can differ from the time sample of digitization of information. This step realizes a fine step of amplitude histograms after the summation of information and induces a precision of a phase adjustment of signals from different receive array individual elements. It is possible to fit these histograms by some function, for example, a sine-function and obtain very small steps in the change of the beam scan angle, up to the size of the screen pixels. It will not increase the angular resolution, which is defined by the width of the beam. But the quality of the image will be increased, because the density of acoustic lines will be high and, respectively, image will be smoother.

Synthetic receive apertures are the same for different sets of information registered from the different flat acoustic beams. A summation of the digitized information for each part of the information map is done after adjustment of the synthetic receive apertures. SUM1, SUM2 and SUM3 (see FIG. 2) are obtained by the summation of column information for different transmit array pulses.

Figure 3:
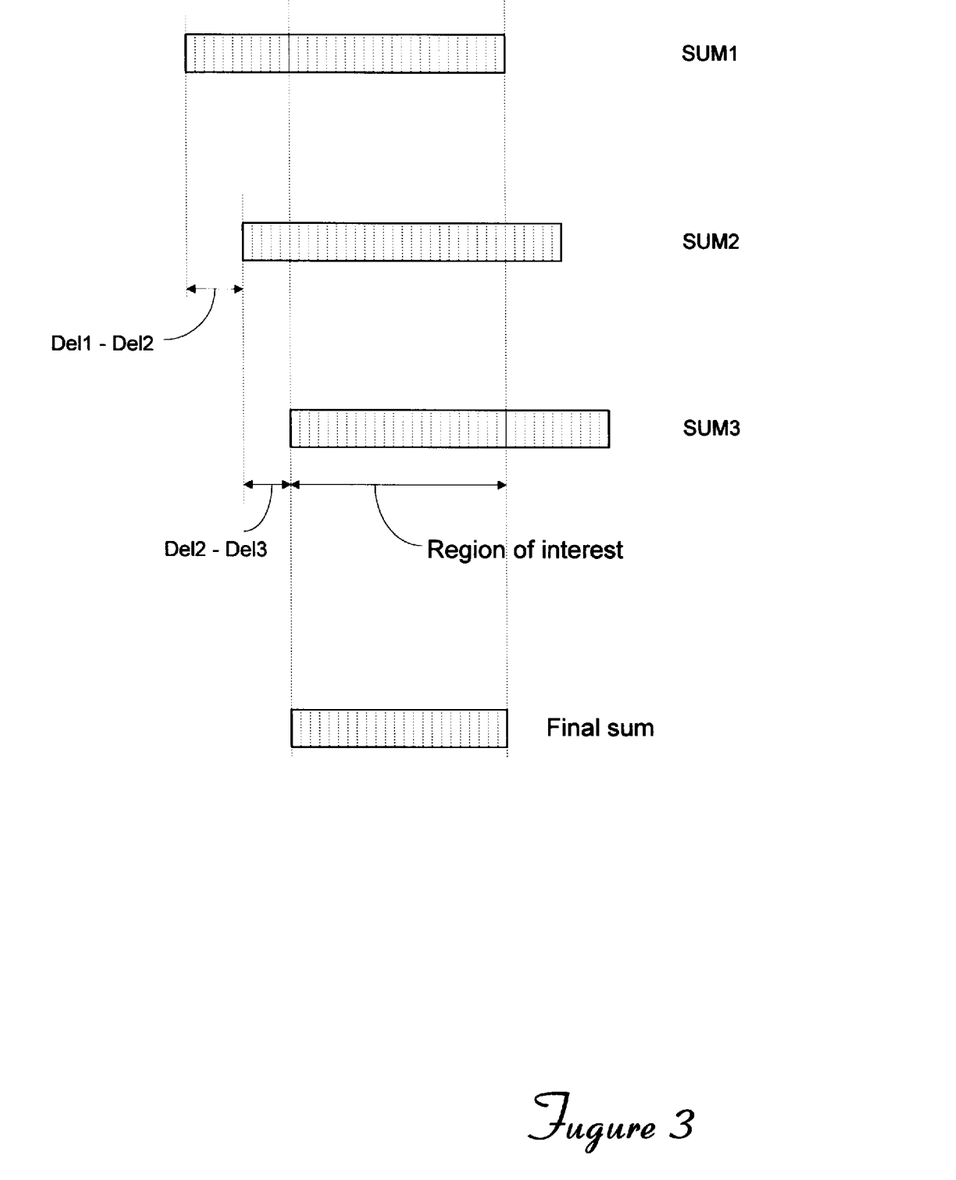
FIG. 3 presents the next transformation of the information map: a creation of the synthetic transmit aperture and a formation of a part of the acoustic line by the summation of digitized information into a region of interest near set focal point.

Third step of realization of the method is shown at FIG. 3: this is a creation of the synthetic transmit aperture for a set focal distance. Sums recorded from different transmit array pulses are shifted relatively each other for the number of time samples equal to the difference of the transmit array delays for a set focal distance. These shifts are equal to Del1–Del2 between first and second transmit arrays and Del2–Del3 between second and third transmit arrays and have a step equal to the fine step of SUM1, SUM2 and SUM3. Values of Del1–Del2 and Del2–Del3 should be calculated before for every scan angle.

A last step of realization of the suggested method is a summation of the amplitude information along the columns of SUM1, SUM2 and SUM3 and obtaining a final sum for the region of interest which corresponds to the part of acoustic line near the set focal point. The time length of an acoustic line part corresponds to a width of the receive zone.

A registration of the part of the acoustic line for the next scan angle realizes by the change of the synthetic receive apertures and values of the (DEl1–Del2) and (Del2–Del3) and consequent summation of column amplitude information.

A direction of a formation of an acoustic line can be changed from usual method when it is comprised from parts shaped for different transmit zones to a circle shape with radius equal to the focal distance of synthetic receive aperture. Such a shape of acoustic lines can make easier the joining of parts of two dimensional images into a common image without the problem of the boundaries between different transmit zones.

These options are repeated for all scan angles allowed by the transducer and for the other receive zones. All these acts are done into memory by the shift of row amplitude information from receive array individual elements for the set transmit zone. The number of acoustic pulses necessary for registration of this information equal to the number of transmit arrays. As a result, a part of two dimensional image of the irradiated sector of a human body corresponds to the set transmit zone will be reconstructed.

The same steps should be done to reconstruct other parts of acoustic image for other transmit zones. Two dimensional acoustic images for other transmit beam scan angles are reconstructed by the same way. Obtained two dimensional acoustic images can be used for reconstruction of three dimensional acoustic images which can be displayed after analysis as some volume pictures or by a sequential display of reconstructed two dimensional images.

If we use more than one receive arrays for a reception of echo signals, every set of information from the different transmit array pulses will contain some subsets of information corresponding to the digitized amplitude information registered by every receive array. In this instance, we need to realize an additional step in the acquisition of a part of an image. After the shaping of the synthetic receive apertures for every subset of the information map, the subsets should be shifted by a calculated time relative to each other the same as it will be done during the form of the synthetic transmit aperture. The summation (SUM1, SUM2, . . . ) should be done along the columns of the subsets of the different receive array information. The steps of the formation of a synthetic transmit aperture and a final summation are the same in this case as described above.

Thus, the suggested fast method of two dimensional acoustic image acquisition allows us to keep a property of a flat beam generation and irradiation of the sector of the investigated part of a human body by the single transmit array. Simultaneously, a switching of transmit (or receive) arrays and irradiation of the same sector of a human body by different transmit arrays with a consequent shifting and summation of the digitized information in the region of interest provides an additional focusing of the transmit (or receive) beam along the coordinate parallel to the flat beam plane. It rejects the level of the side lobes peak amplitudes. Besides, the use of some number of the transmit and receive arrays increase the radiated acoustic power and, respectively, signal/noise ratio. Additionally, a switching of transmit and receive arrays reduces the number of transmit generators and reception channels. If circuitry for switching of the transmit and receive arrays is placed in the handle of the transducer, the number of wires can also be rejected sufficiently.

Some versions of cross transducers which can be used for realization of the suggested fast acoustic image acquisition method are presented at the next Figures of the invention description. The transmit and receive arrays of transducers are manufactured from piezo electric material. Every transmit and receive array individual element has a signal electrode on one side and ground electrode on the opposite side. Transmit and receive arrays are separated completely including the ground electrodes which are joined together in the subsequent apparatus. Transmit array individual elements connect with a pulse driver through multi position switches which provide the sequential generation of the acoustic pulses by the different transmit arrays. Receive array individual elements are connected with the reception part of the apparatus through multi position switches or a cross point switch and provide only the reception of the reflected pulses.

Figure 4:
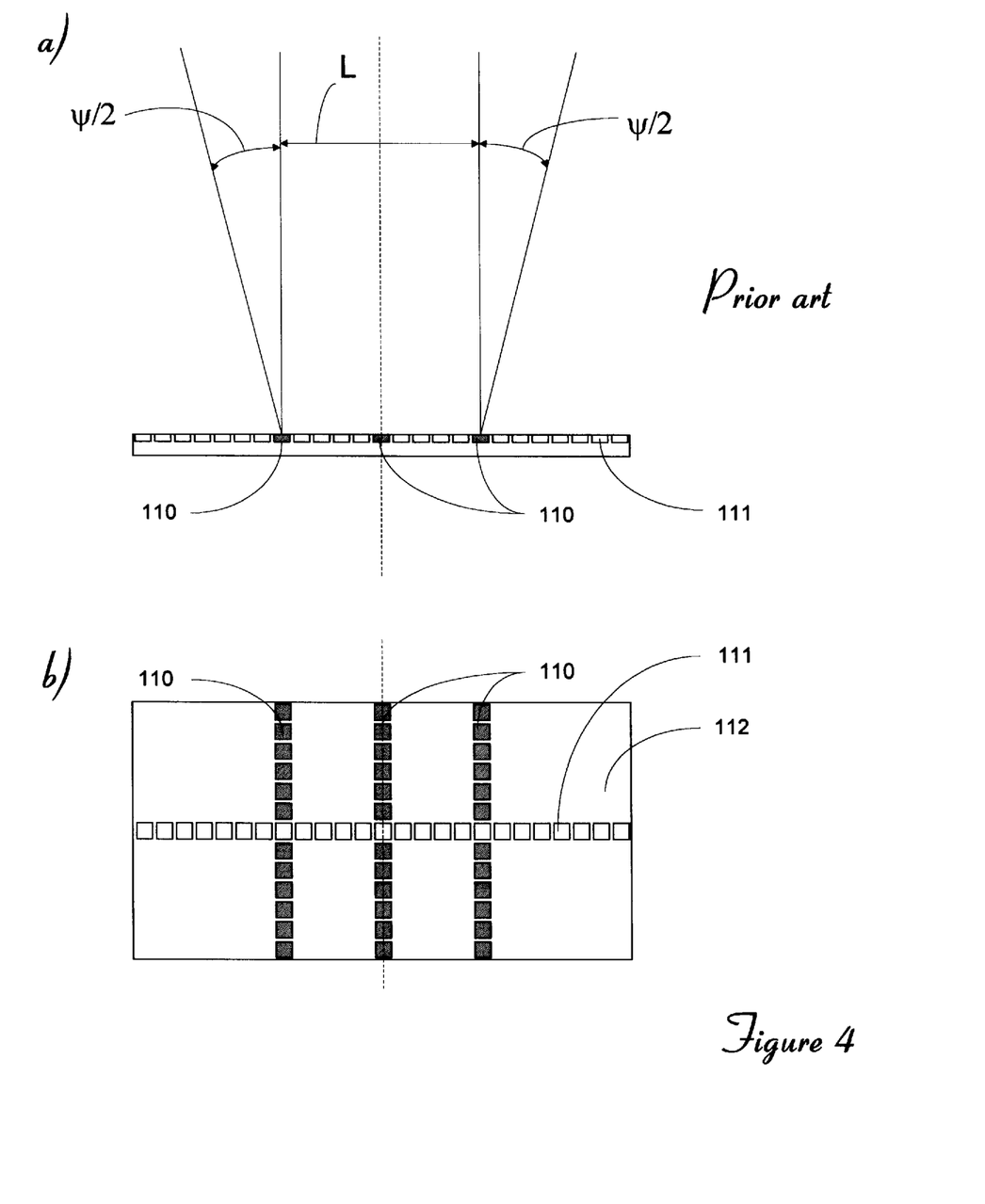
FIG. 4 shows a prior art cross transducer with parallel transmit arrays.

FIG. 4 shows an exemplary view of the prior art cross transducer. It has some number of the transmit arrays 110 and one or more receive arrays 111 placed normally to transmit arrays on the body 112 of the transducer. If the distance between the transmit arrays will be on the order of one wavelength of a generated acoustic frequency, we can realize the fast method of two dimensional image acquisition and the three dimensional image reconstruction with such a scheme for the transducer. The level of the radiated acoustic power and signal/noise ratio will be increased by the use of some number of transmit and receive arrays.

Figure 5:
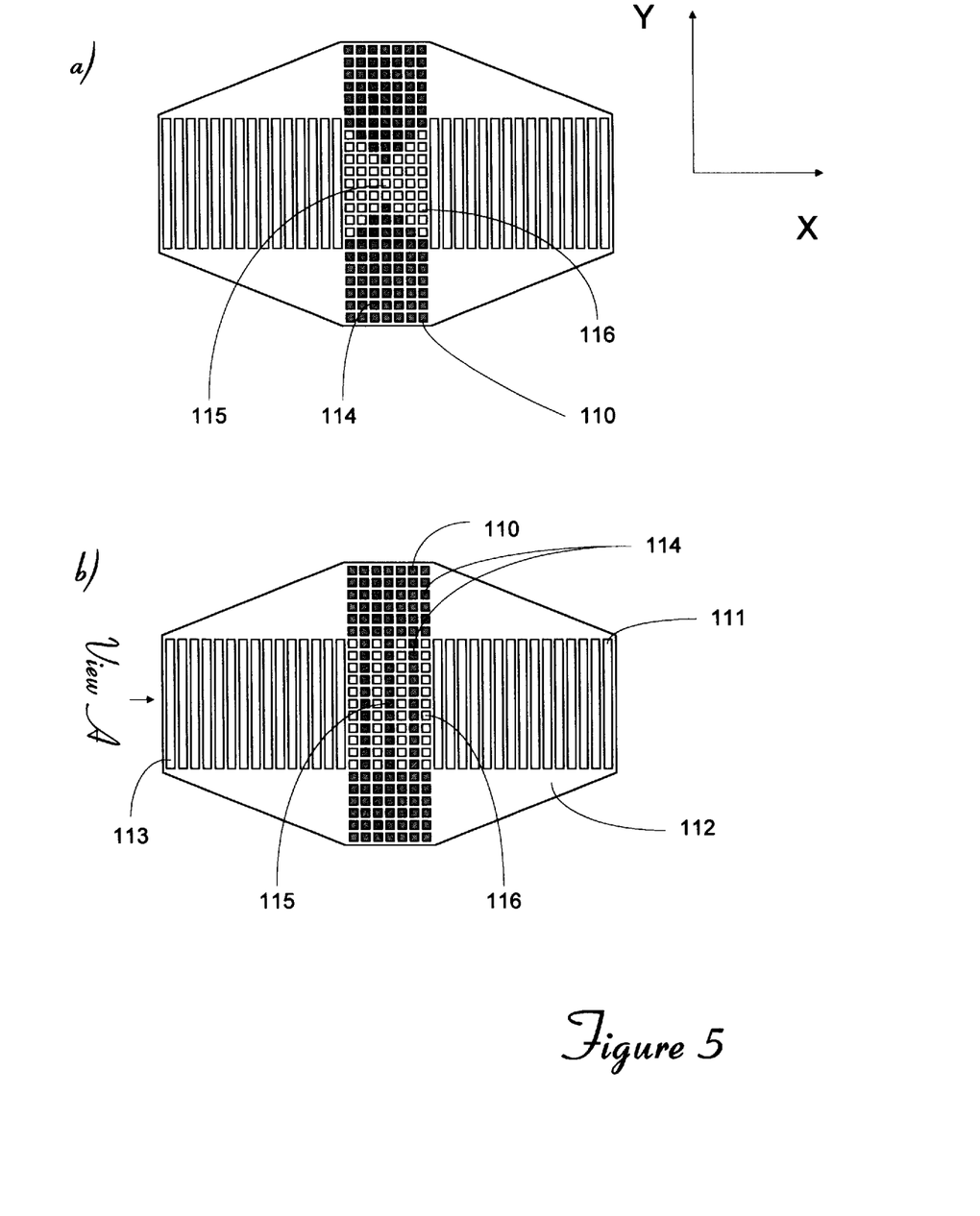
FIG. 5 (a and b) presents the transducer versions for two dimensional images reconstruction with the increased ability to radiate greater power acoustic beam and developed surface of the receive array individual elements.

Further increase of the signal/noise ratio can be obtained by the use of the transducer designs are shown at FIG. 5. They have some number of transmit arrays 110 having individual elements 114 with the same size along both X and Y coordinates and one receive array 111 placed on the body 112 of the transducer along X axis. Receive array individual elements 113 have rectangular shape developed along the elevation coordinate Y. This step increases an amplitude of received echo signals.

Exemplary view of the transducer with a complex geometry of the central intersection area is shown at FIG. 5.a. The intersection area 115 is divided into four sectors. The receive individual elements 116 are placed in two opposite sectors adjacent to the left and right parts of the receive array 111. The signal electrodes of the receive individual element columns are joined and columns are used as single rectangular elements. Common ground electrodes of columns are joined with each other and with the ground electrodes of the left and right parts of receive arrays, and separated from the common transmit ground electrode. Transmit elements 114 placed in the sectors adjacent to the top and bottom parts of transmit arrays 110 are used as single individual elements of transmit arrays. Ground electrodes of transmit arrays are joined into the common transmit ground electrode.

The transducer shown in FIG. 5.b has an intersection area 115 with the same size of transmit 114 and receive 116 array individual elements. The columns of receive individual elements 116 are alternated with columns of transmit individual elements 114. Signal electrodes of receive element columns are joined and every column works as a single individual element. Ground electrodes of receive element columns are joined with adjacent columns and with left and right main parts of the receive array 111, and form a common ground receive electrode separated from the common ground electrode of the transmit arrays.

Figure 6:
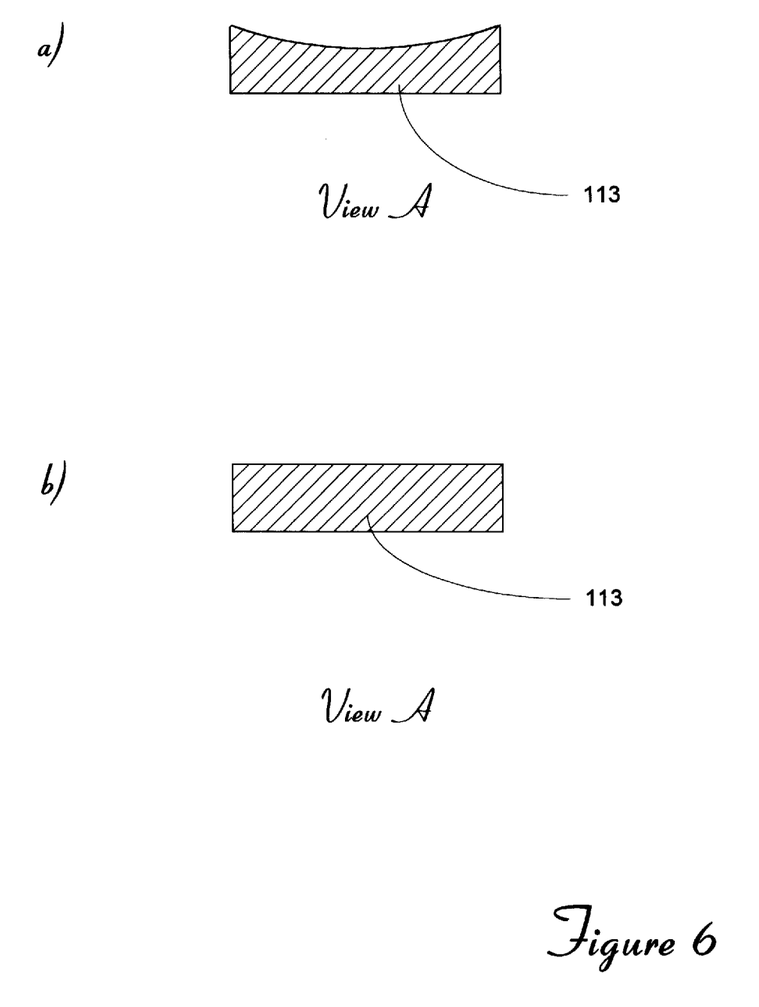
FIG. 6 shows the cross section of the receive array individual elements for cross transducer with developed surface of the receive array individual elements.

FIG. 6 shows a side view of the cross section of the receive array elements used in the transducer design above. It can have a rectangular shape or have some mechanical radius for additional focusing of receive apertures along the elevation coordinate.

The schematics of transducers as described above can be used for the registration of two dimensional images only. The size of the individual elements of the transmit arrays allows the scanning of radiated flat acoustic beams along the elevation coordinate and the dynamic focusing of the beams along the depth coordinate. The rectangular shape of the receive array individual elements provides some focusing of receive apertures along the elevation coordinate, but excludes the possibility of creating flat receive apertures scanned along the elevation coordinate and the registration of three dimensional acoustic images.

What is claimed is:

1. A method for a fast acquisition of two dimensional images comprising the steps of:

a shaping of more than one dynamically focused and scanned flat transmit acoustic beams in a same plane by the energizing of separate parallel phased transmit arrays, which generate their flat beams in time succession and irradiate a same sector of an investigated part of a human body, and which means said flat transmit acoustic beams can be focused and steered by changing the time of an individual transmit array element energizing, a reception of a echo pulses by one or more phased receive arrays placed in parallel, with dynamic focused and scanned flat beam apertures, which means said receive flat beam apertures can be focused and steered by the change in delay of the signals received by individual elements of receive arrays or can be formed by a shifting of a digitized amplitude information in memory for a predetermined number of digits in accordance with the set flat receive aperture, a placement of said separate parallel phased transmit arrays and phased receive arrays at some angle relative to each other, an amplification of the acoustic echo pulses received by the receive array individual elements, a digitization of received amplitude information by a fast amplitude digital converters, a storage of the amplitude and a time digital information from different transmit array pulses in memory as separate sets of information, a formation of synthetic receive apertures for a set focal distance and for the different transmit array pulses by a fine shift of the receive array individual element digital information for the predetermined number of digits corresponding to the predetermined delays necessary for shaping dynamic focused and scanned receive apertures, a summation of said receive array individual element digital information along the columns and with a fine step in a region near a set focal point for sets of an information map from said different transmit array pulses and a storage of obtained sums in memory, a formation of synthetic transmit apertures for a set focal distance by a fine shift of a sum information recorded from the different transmit array pulses for the predetermined number of digits corresponding to the predetermined difference of delays between the same numbers of transmit array individual elements for a set scan angle, a summation of said sum information recorded from the different transmit array pulses in the region of interest for every time point and creation of a part of an acoustic line for the set focal distance and scan angle, a shaping of said synthetic receive and transmit apertures for other scan angles and a creation of parts of other acoustic lines by the fine shift and summation of said receive array individual element digital information and sum information recorded from the different transmit array pulses for other scan angles and recording of a part of two dimensional image in memory, a generation of flat acoustic beams with other focal distances in succession , a reception of echo signals by receive array individual elements, an amplification, a digitization and storage of said receive array individual element digital information in memory, an acquisition of parts of acoustic lines and two dimensional images by the shaping of said synthetic receive and transmit apertures for different scan angles and for other focal distances, by the fine shift and summation of said receive array individual element digital information and sum information recorded from the different transmit array pulses for different scan angles, recording of a part of a two dimensional image for other transmit focal distances in memory and reconstruction of two dimensional image from registered and stored parts, whereby said fast acquisition of two dimensional images is provided by a generation of the flat transmit beams in series at the same plane and irradiation of the same sector of an investigated part of a human body, a creation of said synthetic receive and transmit apertures for a set transmit zones by a fine shift and summation of digital information recorded from the different transmit array pulses for different scan angles and for other transmit focal distances in memory and reconstruction of two dimensional image from registered and stored parts.

2. An ultrasound cross transducer for fast acquisition of two dimensional images comprising:

more than one of transmit arrays placed in parallel to each other and having a plurality of individual elements, every said element has a signal electrode on one side of a piezo electric material and a ground electrode on the opposite side, said individual elements are connected with a pulse driver through the multi position switches and provide only the emitting of the acoustic wave pulses into an irradiated sector of a human body by the energizing of different transmit arrays in succession, one receive array having a plurality of rectangular individual elements oriented along an elevation coordinate, each said element has a signal electrode from one side of the piezo electric material and a ground electrode from the opposite side, said individual elements are connected with reception apparatus only, which provides a reception of the echo signals from the individual elements of receive array, an amplification, a digitization and a memorization of echo signals amplitudes, said transmit arrays and receive array are oriented relative to each other at some angle, said transmit arrays provide the generation of their own flat acoustic beams in the same plane and an irradiation of the same sector of a human body, and can be dynamically focused and scanned by the adjustment in time of the generated acoustic pulses from each individual element of the arrays, said transmit arrays are separated from said receive array including a separation of the ground electrodes.

3. An ultrasound cross transducer as recited in claim 2 having an intersection area divided for four sectors with transmit and receive individual elements placed in two opposite sectors adjacent to a top and a bottom parts of transmit arrays and a left and a right parts of receive array, signal electrodes of the receive element columns are joined and every column works as single individual element, ground electrodes of transmit array individual elements are joined with transmit ground electrode, ground electrodes of receive array individual elements are joined with receive ground electrode.

4. An ultrasound cross transducer as recited in claim 2 having an intersection area with a same size of transmit and receive individual elements, the columns of the receive individual elements are alternated with columns of the transmit individual elements, signal electrodes of the receive element columns are joined and every column works as a single individual element, ground electrodes of transmit array individual elements are joined with a transmit ground electrode, ground electrodes of receive array individual elements are joined with a receive ground electrode.

* * * * *